US008170638B2

(12) United States Patent
Nishida et al.

(10) Patent No.: US 8,170,638 B2
(45) Date of Patent: May 1, 2012

(54) MEMS FLEXIBLE SUBSTRATE NEURAL PROBE AND METHOD OF FABRICATING SAME

(75) Inventors: Toshikazu Nishida, Gainsville, FL (US); Erin E. Patrick, Vero Beach, FL (US); Justin Sanchez, Newberry, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1081 days.

(21) Appl. No.: 11/852,842

(22) Filed: Sep. 10, 2007

(65) Prior Publication Data

US 2009/0299166 A1   Dec. 3, 2009

Related U.S. Application Data

(60) Provisional application No. 60/825,160, filed on Sep. 11, 2006.

(51) Int. Cl.
*A61B 5/04*   (2006.01)

(52) U.S. Cl. .................................... 600/378; 607/116

(58) Field of Classification Search ................. 600/377, 600/378; 607/116
See application file for complete search history.

(56) References Cited

U.S. PATENT DOCUMENTS

| | | | |
|---|---|---|---|
| 4,461,304 A * | 7/1984 | Kuperstein | 600/378 |
| 5,524,338 A * | 6/1996 | Martyniuk et al. | 29/825 |
| 5,897,583 A * | 4/1999 | Meyer et al. | 607/116 |
| 6,171,239 B1 * | 1/2001 | Humphrey | 600/372 |
| 6,368,147 B1 * | 4/2002 | Swanson | 439/496 |
| 6,829,498 B2 * | 12/2004 | Rousche et al. | 600/378 |

OTHER PUBLICATIONS

Stieglitz et al, "Flexible, Polyimide-Based Neural Interfaces", Seventh International Conference on Microelectronics for Neural, Fuzzy and Bio-Inspired Systems, 1998.*
Patrick, et al., "Design and Fabrication of a Flexible Substrate Microelectrode Array for Brain Machine Interfaces," University of Florida, Gainesville, FL.
Patrick, et al., "Electrochemical Impedance Spectroscopy of Neural Probe Polymer Insulation," University of Florida, Gainesville, FL.
Takeuchi, et al., "3D Flexible Multichannel Neural Probe Array," J. Micromech. Microeng. 14 (2004) 104-107.

* cited by examiner

*Primary Examiner* — Lee Cohen
(74) *Attorney, Agent, or Firm* — Thomas, Kayden, Horstemeyer & Risley, LLP

(57) ABSTRACT

A method of fabricating a MEMS flexible substrate neural probe is provided. The method can include applying an insulation layer on a substrate, and depositing a plurality of metal traces on the insulation layer and electroplating each of the plurality of traces. The method also can include encapsulating the insulation layer and metal traces deposited thereon with an insulation layer. Additionally the method can include etching the insulation layer to form a plurality bond pad sites and probes to form a flexible ribbon cable having a plurality of bond pad sites disposed on a surface of the flexible cable and a plurality of neural probes extending from the flexible cable. The method further can include separating the substrate from the insulation layer and depositing insulation on each of the neural probes, each probe comprising insulated portion and exposed metallic tip. Moreover, the method can include cutting each of the exposed metallic tips, and plating each of the exposed metallic tips and each of the plurality of bond pad sites.

10 Claims, 5 Drawing Sheets

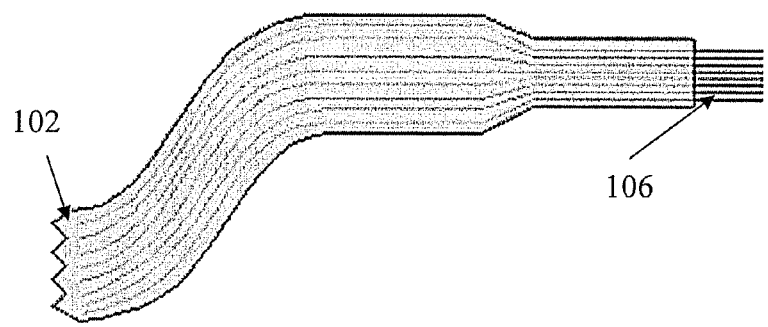
FIG. 1
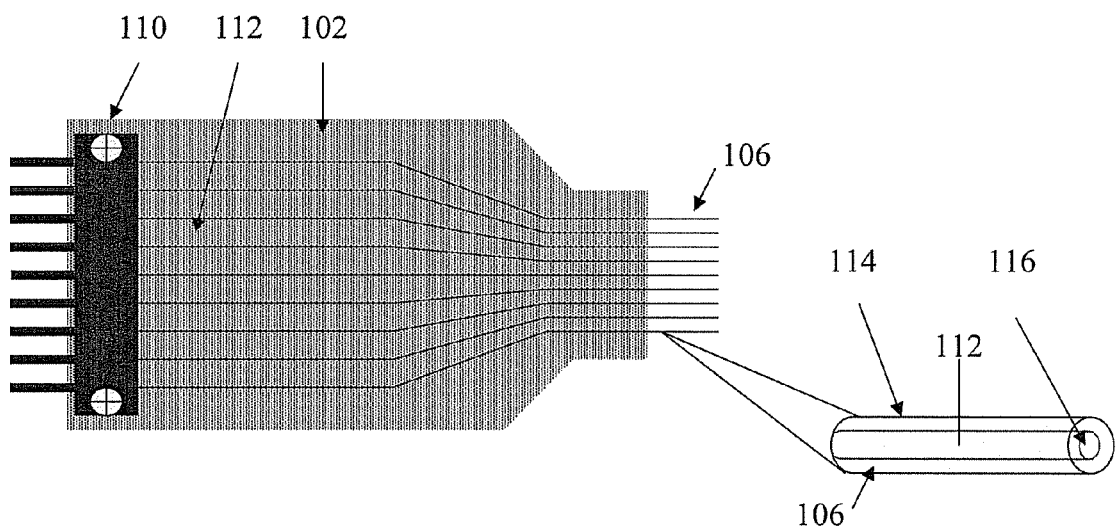
FIG. 2  FIG. 3

MEMS FLEXIBLE SUBSTRATE NEURAL PROBE AND METHOD OF FABRICATING SAME

CROSS-REFERENCE TO RELATED APPLICATIONS

The present application claims the priority of U.S. Provisional Application Ser. No. 60/825,160 filed on Sep. 11, 2006 and incorporated herein by reference in its entirety.

STATEMENT REGARDING FEDERALLY SPONSORED RESEARCH OR DEVELOPMENT

The United States Government may have certain rights in the invention by virtue of support provided by the United States Department of Defense Advanced Research Projects Agency under a grant designated DARPA/#N66001-02-C-8022.

FIELD OF THE INVENTION

The present invention is related to the field of electronic probes, and, more particularly, to micro electromechanical system (MEMS) probes that interface with neurons of the nervous system of a biological entity.

BACKGROUND OF THE INVENTION

Microelectrode neural probes provide a direct electrical interface with the neurons of a biological entity's nervous system. Such neural probes can target the neuronal activity of neurons, enabling researchers and clinicians to better explore and understand neurological diseases, neural coding, neural modulations, and neural topologies.

Moreover, the capabilities for analyzing neuronal activity using neural probes has led to the development of new neuro-therapeutic devices implemented through brain-machine interfaces (BMIs) comprising neural probes. An underlying objective in using BMI devices is to bypass damaged tissue through the BMI so that a patient can regain lost communication and/or control with respect to some aspect of the patient's nervous system. Such devices, for example, may restore physical mobility and/or communicative abilities to patients suffering from paralysis due to spinal chord injury, stroke, brachial plexus injury, or similar types of injuries involving the nervous system. Through a BMI a patient, for example, could directly control a prosthetic limb or wheelchair. Similarly, through a BMI the patient could communicate through an external device controlled by the patient.

Typically, with the BMI, signals corresponding to neural activity are chronically collected from the cortex of the patient's brain. The signals are interpreted and, in turn, signals for effecting a needed therapy are delivered through the interface. Accordingly, an important objective with the BMI is a capability for acquiring, via the interface, sufficiently discernable neural signals. This typically requires that electrodes of the BMI be inserted into the cortical tissue of a patient's brain with the sufficient spatial resolution needed to record action potentials from individual neurons.

Generally, there are two principal types of fixed neural probes that are commonly used for recording neural signals. One type is a neural probe using wire microelectrode neural probes assembled from insulated tungsten wires. The other type is a neural probe using micro-machined electrodes fabricated using conventional integrated circuit (IC) micro-fabrication technologies.

Wire microelectrodes can provide precise signal "firing" information with respect to individual neurons in the cortical and sub-cortical tissues. Micro-wire electrodes typically comprise bundles of tungsten wires having diameters of 50 µm and electro-polished tips, either blunt or sharpened. Fabricating arrays of microelectrodes for chronic use has proved a particular challenge since the arrays are typically assembled from discrete components. Moreover, the array layout, particularly inter-electrode spacing and electrode morphology are usually not uniform because the arrays are constructed from drawn strands of wire.

The second type of fixed neural probe was devised in an attempt to overcome the inherent challenges with respect to the first type by utilizing micro-fabrication and micro-machining techniques typically employed with IC fabrication. This second type of fixed neural probe is fabricated using photolithography to transfer electrode patterns. Silicon electrode shanks can be fabricated through selective etching using impurity etch stops in concert with anisotropic liquid etchants as well as anisotropic dry etches. It also is possible to interpose signal processing circuitry onto the substrate of the probe. Signal recording sites of such probes typically comprise exposed metal pads located on rigid shanks that are connected, via interconnection traces, to output leads or to signal processing circuitry on a monolithic substrate.

Some neural probes are fabricated to include multiple recording sites placed along the length of the shank to enable signal interrogation of cells at varying depths of the neural tissue. The added wiring required, however, can increase the thickness of the electrode shanks up to approximately 160 µm, which increases the risk that insertion of the probe could injure a patient's brain tissue. Another approach is to fabricate the neural probe with internal circuitry to multiplex the electrodes, thereby facilitating added numbers of recording electrodes without undue increases in shank dimensions. The added circuitry, however, can increase the complexity of the fabrication process.

Another concern regarding rigid-substrate, micro-machined neural probes is that the probes are subject to mechanical forces owing to strain that transfers from the mount to the probes as they "float" in neural tissue, thereby creating the risk for reduced reliability of the probe resulting from injury to the tissue. One approach intended to mitigate this risk is to make the substrate of the microelectrode array flexible by utilizing thin-metal electrode sites and enclosing the wiring between polymer materials. The resulting electrode array is completely flexible, thereby providing needed strain relief. However, this design prevents direct insertion of the probe into brain tissue. Instead, with this type of probe, an incision much be first created to effect implantation. This typically results in increased tissue damage. An alternative is to use a complex design of rigid probes with planar electrode sites on the probe shank and a flexible cable to connect electrodes to output ports.

As yet, however, there is not a flexible neural microelectrode array design that provides a good compromise between the best properties of micro-wire electrodes and MEMS fabrication techniques. More generally, there is as yet a need for an electrode array that can achieve high neuronal yield that is highly customizable in terms of geometry/layout, that can mitigate tissue damage during implantation, and that also can be relatively easily and efficiently fabricated in large numbers.

SUMMARY OF THE INVENTION

The invention is directed to a flexible neural microelectrode array, defining a flexible neural probe. The invention is also directed to the fabrication of a flexible a neural probe.

One embodiment of the invention is a MEMS flexible substrate neural probe. The neural probe can include a micro-machined flexible ribbon cable comprising a plurality of small-profile metal traces enclosed within a flexible insulation material. The neural probe further can include an array of needle-like probes extending outwardly from the flexible ribbon cable. Each such needle-like probe can comprise an elongate conductor substantially enclosed by a surrounding insulator and having an exposed tip.

Another embodiment of the invention is a method of fabricating a MEMS flexible substrate neural probe. The method can include applying an insulation layer on a substrate, and depositing a plurality of metal traces on the insulation layer and electroplating each of the plurality of traces. The method also can include encapsulating the insulation layer and metal traces deposited thereon with an insulation layer. Additionally the method can include etching the insulation layer to form a plurality of bond pad sites and probes to form a flexible ribbon cable having a plurality of bond pad sites disposed on a surface of the flexible cable and a plurality of neural probes extending from the flexible cable. The method further can include separating the substrate from the insulation layer and depositing insulation on each of the neural probes, each probe comprising an insulated portion and exposed metallic tip. Moreover, the method can include cutting each of the exposed metallic tips, and plating each of the exposed metallic tips and each of the plurality of bond pad sites.

BRIEF DESCRIPTION OF THE DRAWINGS

There are shown in the drawings, embodiments which are presently preferred. It is expressly noted, however, that the invention is not limited to the precise arrangements and instrumentalities shown.

FIGS. 1 and 2 are perspective views of a MEMS flexible neural probe, according to an embodiment of the invention.

FIG. 3 is a perspective view of an end portion of a probe of the MEMS flexible neural probe shown in FIG. 1.

DETAILED DESCRIPTION

Figure 4A:
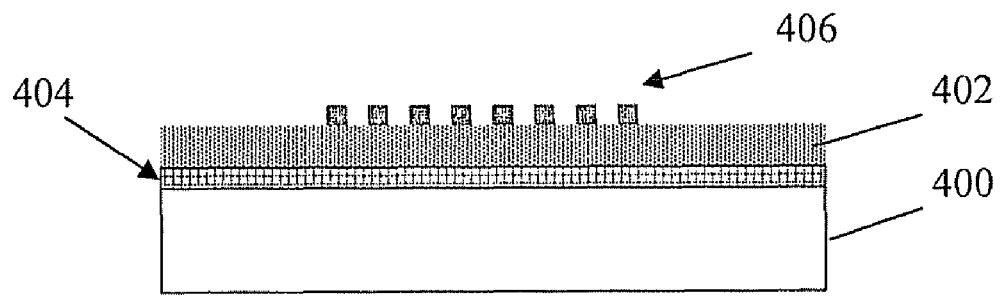
FIGS. 4(a)-(c) are schematic views of a substrate at different stages during a process for fabricating a MEMS flexible neural probe, according to an embodiment of the invention.

The invention is directed to the design and fabrication of a flexible neural microelectrode array, defining a neural probe. As described herein, the neural probe according to the invention combines properties of micro-wire electrodes and micro electromechanical system (MEMS) fabrication techniques. The neural probe can achieve high neuronal yield, is highly customizable with respect to its geometry and layout, and can be readily implanted into biological tissue. Moreover, the neural probe can be fabricated readily and efficiently on a mass scale.

Referring initially to FIGS. 1 and 2, a MEMS flexible neural probe 100 according to one embodiment of the invention is shown. The neural probe 100 illustratively includes a flexible ribbon cable 102, formed from a substrate as described below. At least one bond pad site (not shown) can be disposed on the flexible ribbon cable 102. Additionally, the neural probe 100 illustratively includes a plurality of neural probes 106 extending outwardly from the flexible ribbon cable 102. As explicitly shown in FIG. 2, an external connector 110 can connect to an end of the flexible ribbon cable 102 opposite the end from which the neural probes 106 extend.

As described more particularly below, the neural probe 100 is preferably fabricated using known micro-machining techniques. Specifically, the flexible ribbon cable 102 can be fabricated by enclosing small-profile metal traces 112 between a flexible insulating material on a substrate, and by micro-machining the material to produce a micro-machined flexible ribbon cable of a desired precision. As described more particularly below, the small-profile metal traces are preferably formed of nickel (Ni) or platinum (Pt). The plurality of neural probes 106 thus can comprise an array of needle-like probes that are formed by etching a predetermined amount of the insulation from an end portion of the substrate from which the flexible ribbon cable 102 is formed so as to expose the needle-like probes.

In forming the neural probes 106, all but the tips of the protruding, needle-like probes can be insulated by depositing a layer of vapor-deposited insulation on each probe so that only the tips are exposed, thus yielding a discriminating recording sites of the neural probe 100. The sites can be micro-machined to be 20×50 µm to effect a good compromise between signal selectivity and noise performance.

Referring additionally to FIG. 3, a perspective view of one of the neural probes 106 is provided. Each of the plurality of neural probes 106 comprises an insulated shank formed by a wire extension of the small-profile metal trace 112 surrounded by insulation 114. According to one embodiment, the insulation material that insulates each shank is a flexible polyimide. Preferably, the insulation is parylene-C insulation.

As further illustrated, an exposed end portion of each of the neural probes 106 comprises an electroplated probe tip 116. Preferably gold (Au), and more preferably platinum (Pt), is electroplated on the probe tip 116. The neural probes 106 can be fabricated such that the probe tips 116 are tapered to a width of 4 µm in width, with the height determined by the electroplating time. For best signal acquisition in terms of an optimum signal-to-noise ratio, an area of 20×50 µm$^2$ is preferred. In general, however, the probe tips can be fabricated over a range of dimensions (e.g., 4 µm to 100 µm width or height). The dimension can be selected to provide an electrode area that has the best signal-to-noise ratio.

Figure 4B:
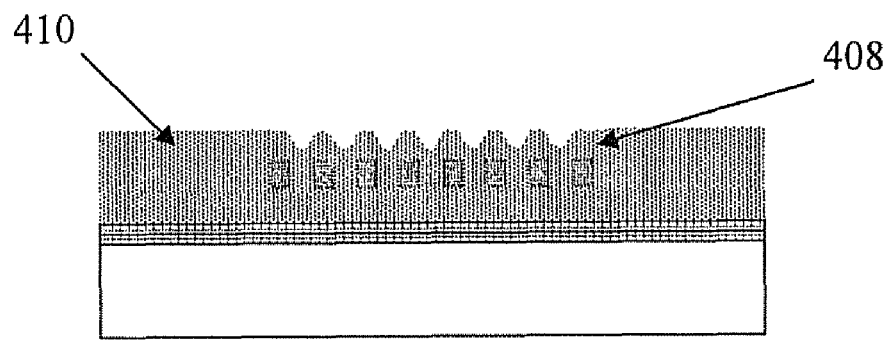

FIGS. 4(a)-(e) provide schematic views of a substrate at different stages during a process for fabricating a MEMS flexible neural probe, according to another embodiment of the invention. In FIG. 4(a), the substrate 400 is a silicon (Si) substrate obtained from a silicon wafer. On the substrate 400, is a layer of cured polyimide 402, which is illustratively connected to the substrate by a layer of Kapton tape 404. Metal traces 406, such as nickel (Ni), are sputtered and patterned on the cured polyimide 402. The traces 406 are then electroplated to final height. As shown in FIG. 4(b), wiring 408, such as nickel, is then encapsulated in a top layer of polyimide 410.

Figure 4C:
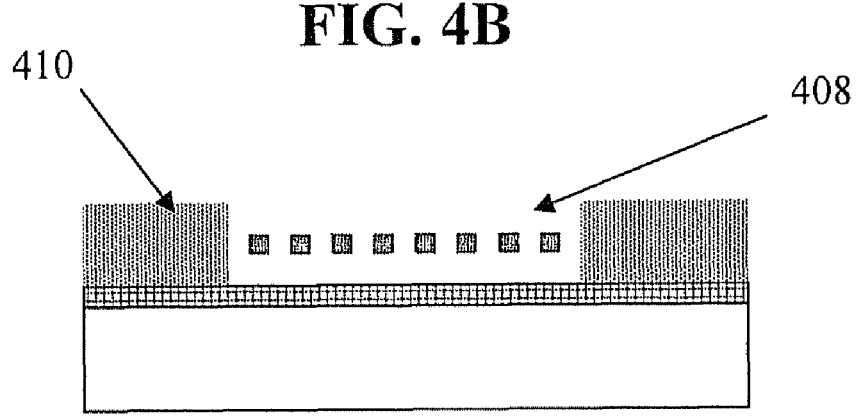

The above-described bond pad sites and neural probes are then formed by etching the surface of the polyimide 410, as schematically shown in FIG. 4(c). Etching can be effected, for example, through reactive ion etching (RIE), which, as will be readily understood by one of ordinary skill in the art, is a form of dry etching in which ions are targeted at a surface, and etching is effected as reactive ions are accelerated in the direction of the surface that is to be etched.

Figure 4D:
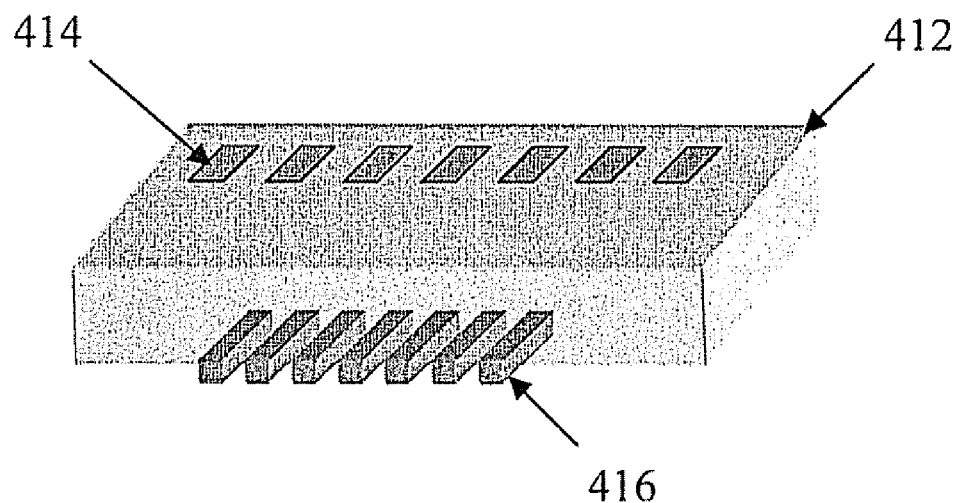
FIGS. 4(d) and (e) are perspective views of the MEMS flexible neural probe at additional stages during the process for fabricating a MEMS flexible neural probe, according to an embodiment of the invention.

FIG. 4(d) is a perspective view of the neural probe at this point of the process of fabrication. The substrate 400 is diced, and the structure resulting from the preceding steps is removed from the substrate. As illustrated, the structure comprises a flexible ribbon cable 412. Bond pad sites 414 are formed on a surface of the flexible ribbon cable 412. The plurality of neural probes 416 extend outwardly from the flexible ribbon cable 412.

Figure 4E:
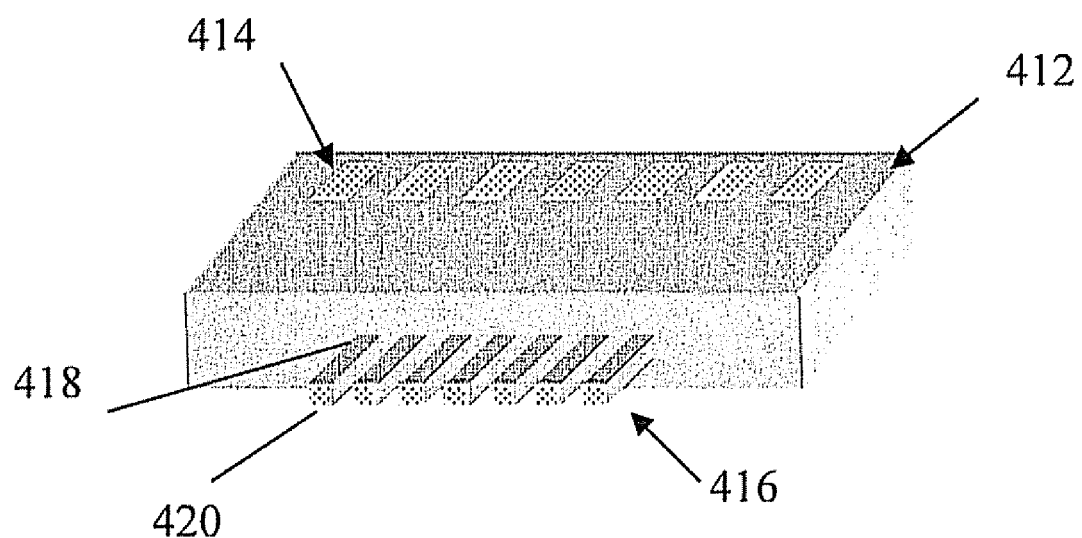

FIG. 4(e) is a perspective view of the neural probe at the final stage in the fabrication process. An insulation 418, such as the aforementioned parylene-C, is deposited on the structure by vapor deposition. The tips 420 of the neural probes are formed by machine cutting an end portion of each of the neural probes 416 extending outwardly from the flexible ribbon cable 412. Lastly, both the tips 420 and the bond pad sites 414 are electroplated.

Figure 6:
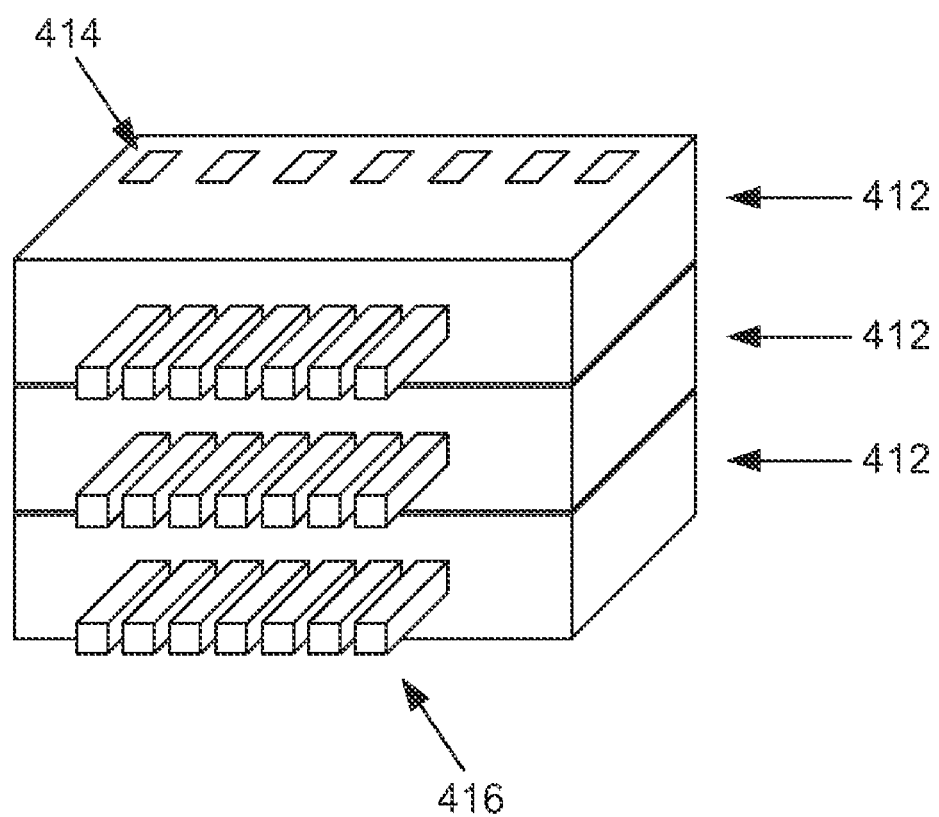
FIG. 6 is a perspective view of a plurality of stacked arrays.

In alternative embodiments of the invention, the earlier-described array of the neural probe comprises a plurality of planar arrays. The planar arrays can be stacked relative to one another to form a three-dimensional (3-D) arrangement or geometry. The planar arrays can be variously arranged to form different geometries. Accordingly, the stacked planar arrays are customizable. A customized 3-D array, more particularly, can be tailored to accommodate a particular neural structure with which the neural probe is to be used. Thus, according to another embodiment of the invention, the neural probe comprises a plurality of planar arrays stacked to form a customizable three-dimensional (3-D) arrangement, the 3-D arrangement having a geometry suited to a particular, predetermined neural structure (see FIG. 6).

Figure 5:
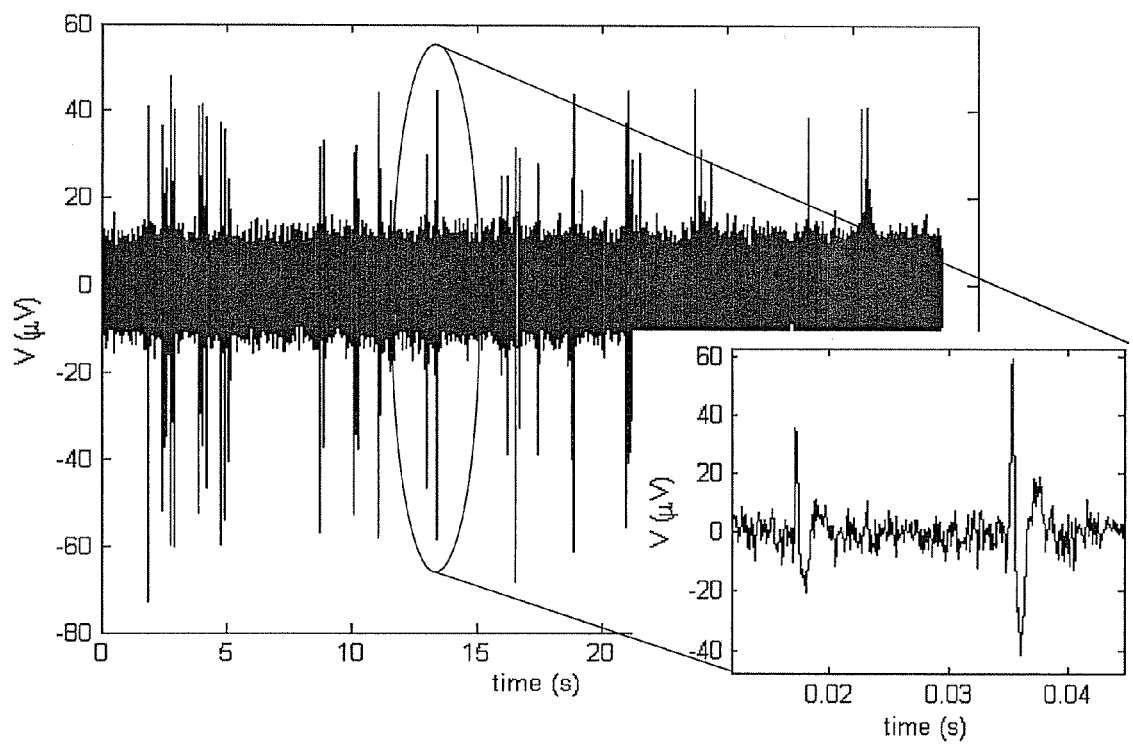
FIG. 5 is a plot of neural recordings obtained using the MEMS flexible neural probe shown in FIG. 1.

FIG. 5 is a plot of data obtained from implanting a physical embodiment of the flexible substrate neural probe described herein into the forelimb region of the primary cortex of an anesthetized laboratory rat. The flexible substrate neural probe was implanted at depth of 1.66 mm within the primary cortex. In vivo recordings obtained during the procedure are shown by the plot of data in the figure. The data maps the recorded voltages, in micro-voltages, against time, in seconds. The figure insert shows the recording of two distinct neurons recorded by a single probe, which reveals peak-to-peak amplitudes of 53 μV and 85 μV for the two distinct neurons.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A MEMS flexible substrate neural probe for use with the brain, comprising:
    a micro-machined flexible ribbon cable comprising a plurality of small-profile metal traces enclosed within a flexible polymeric insulation material; and
    an array of needle-like probes extending outwardly from an end of the flexible ribbon cable, each probe comprising an elongated conductor and an insulator that surrounds the entire length of the conductor except for its distal tip so that only the tip of the conductor is exposed to enable recording of data from a discrete point within the brain.

2. The neural probe of claim 1, further comprising a plurality of bond pad sites disposed on a surface of the flexible ribbon cable.

3. The neural probe of claim 1 wherein the flexible polymeric insulation material comprises polyimide insulation material.

4. The neural probe of claim 1, wherein the insulator comprises parylene-c.

5. The neural probe of claim 1, wherein each distal tip of the array is micro-machined to have cross-sectional areas of less than 20×50 μm².

6. The neural probe of claim 1, wherein each distal tip of the array is electroplated.

7. The neural probe of claim 6, wherein the electroplated distal tip is electroplated with one of gold (Au) or platinum (Pt).

8. The neural probe of claim 1, wherein the small-profile metal traces and conductors of the array comprises one of nickel (Ni) or platinum (Pt).

9. The neural probe of claim 1, wherein each probe of the array is no more than 2 mm in length.

10. The neural probe of claim 1, wherein the array comprises a plurality of planar arrays stacked to form a customizable three-dimensional (3-D) arrangement, the 3-D arrangement having a geometry suited to a predetermined neural structure.

* * * * *